(12) United States Patent
Schwab (10) Patent No.: US 9,277,939 B2
(45) Date of Patent: Mar. 8, 2016

(54) SPINAL CORRECTION SYSTEM AND METHOD

(71) Applicant: Warsaw Orthopedic, Inc., Warsaw, IN (US)

(72) Inventor: Frank J. Schwab, New York, NY (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 119 days.

(21) Appl. No.: 13/629,839

(22) Filed: Sep. 28, 2012

(65) Prior Publication Data

US 2014/0094854 A1 Apr. 3, 2014

(51) Int. Cl.
*A61B 17/70* (2006.01)
*A61B 17/88* (2006.01)

(52) U.S. Cl.
CPC ......... *A61B 17/7004* (2013.01); *A61B 17/7005* (2013.01); *A61B 17/7022* (2013.01); *A61B 17/7032* (2013.01); *A61B 17/7091* (2013.01); *A61B 17/8861* (2013.01)

(58) Field of Classification Search
CPC ............... A61B 17/7037; A61B 17/02; A61B 17/7008; A61B 17/7034
USPC .................................. 606/246–279, 305–308
See application file for complete search history.

(56) References Cited

U.S. PATENT DOCUMENTS

| | | | | |
|---|---|---|---|---|
| 6,280,472 | B1 * | 8/2001 | Boucher | A61B 17/0642 606/323 |
| 7,083,621 | B2 * | 8/2006 | Shaolian | A61B 17/1671 606/256 |
| 8,202,303 | B2 * | 6/2012 | Zehnder | A61B 17/7031 606/264 |
| 8,361,118 | B2 * | 1/2013 | Biedermann et al. | 606/259 |
| 8,366,746 | B2 * | 2/2013 | Kiester | A61B 17/705 606/259 |
| 8,388,658 | B2 * | 3/2013 | Veldman | A61B 17/7004 606/254 |
| 8,425,564 | B2 * | 4/2013 | Kiester | A61B 17/705 606/259 |
| 8,535,351 | B1 * | 9/2013 | Law | A61B 17/7007 606/257 |
| 8,647,354 | B2 * | 2/2014 | Domingo | A61B 17/0469 606/139 |
| 8,652,137 | B2 * | 2/2014 | Blain | A61B 17/1608 606/167 |
| 8,992,533 | B2 * | 3/2015 | Blain | A61B 17/1608 606/79 |
| 2006/0064092 | A1 * | 3/2006 | Howland | A61B 17/7007 606/261 |
| 2007/0179525 | A1 * | 8/2007 | Frecker | A61B 17/29 606/205 |
| 2008/0154308 | A1 * | 6/2008 | Sherman | A61B 17/7008 606/265 |
| 2009/0088799 | A1 * | 4/2009 | Yeh | A61B 17/7005 606/246 |
| 2009/0177232 | A1 * | 7/2009 | Kiester | A61B 17/705 606/260 |
| 2009/0198277 | A1 * | 8/2009 | Gordon | A61B 17/688 606/248 |
| 2009/0248088 | A1 * | 10/2009 | Biedermann | A61B 17/7032 606/305 |
| 2009/0287260 | A1 * | 11/2009 | Zehnder | A61B 17/7032 606/305 |
| 2010/0004686 | A1 * | 1/2010 | Lemoine | A61B 17/705 606/246 |
| 2010/0042155 | A1 * | 2/2010 | Biedermann | A61B 17/7004 606/254 |
| 2010/0087862 | A1 * | 4/2010 | Biedermann | A61B 17/702 606/259 |
| 2010/0106190 | A1 * | 4/2010 | Linares | A61B 17/7065 606/249 |

(Continued)

*Primary Examiner* — Ellen C Hammond
*Assistant Examiner* — Stuart S Bray (57) ABSTRACT

A spinal correction system includes at least one longitudinal element extending between a first portion and a second portion. At least one fixation element includes a first end and a second end that is configured for penetrating tissue. A coupling member is configured for disposal about the at least one longitudinal element. The coupling member includes a first part and a second part being movable relative to the first part between a first orientation and a second orientation such that an inner surface of the parts are fixed with the at least one longitudinal element. The parts include an outer surface such that in the second orientation, the coupling member is configured for a snap fit engagement with the at least one fixation element such that the parts are fixed with the first end. Methods of use are disclosed.

20 Claims, 6 Drawing Sheets

(56) References Cited

U.S. PATENT DOCUMENTS

| | | | |
|---|---|---|---|
| 2010/0331886 A1* | 12/2010 | Fanger | A61B 17/7005 606/264 |
| 2012/0083826 A1* | 4/2012 | Chao | A61B 17/00234 606/205 |
| 2012/0089186 A1* | 4/2012 | Carl | A61B 17/7053 606/249 |
| 2012/0143255 A1* | 6/2012 | Jackson | A61B 17/7004 606/259 |
| 2012/0221059 A1* | 8/2012 | Mollman | A61B 17/7074 606/277 |
| 2012/0265247 A1* | 10/2012 | Biedermann | A61B 17/7031 606/255 |
| 2013/0165002 A1* | 6/2013 | Nooner | H01R 13/516 439/892 |
| 2013/0190823 A1* | 7/2013 | Thompson | A61B 17/702 606/265 |
| 2013/0261668 A1* | 10/2013 | Douget | A61B 17/7032 606/278 |
| 2013/0338714 A1* | 12/2013 | Chang | A61B 17/7017 606/258 |
| 2014/0031868 A1* | 1/2014 | Biedermann et al. | 606/255 |
| 2014/0069904 A1* | 3/2014 | Sammons | H01R 13/502 219/136 |
| 2014/0107709 A1* | 4/2014 | Schmitz | A61B 10/0275 606/279 |
| 2014/0163664 A1* | 6/2014 | Goldsmith | A61B 17/00491 623/1.11 |

* cited by examiner

SPINAL CORRECTION SYSTEM AND METHOD

TECHNICAL FIELD

The present disclosure generally relates to medical devices for the treatment of musculoskeletal disorders, and more particularly to a surgical system and method for correction of a spine disorder.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. Correction treatments used for positioning and alignment may employ implants, such as vertebral rods and bone screws, for stabilization of a treated section of a spine. This disclosure describes an improvement over these prior art technologies.

SUMMARY

Accordingly, a spinal implant system is provided. In one embodiment, the system includes at least one longitudinal element extending between a first portion and a second portion. At least one fixation element is provided that includes a first end and a second end configured for penetrating tissue. A coupling member is provided that is configured for disposal about the at least one longitudinal element and includes a first part and a second part being movable relative to the first part between a first orientation and a second orientation such that an inner surface of the parts are fixed with the at least one longitudinal element. The parts include an outer surface such that in the second orientation, the coupling member is configured for a snap fit engagement with the at least one fixation element such that the parts are fixed with the first end.

In one embodiment, a method for treating a spine is provided. The method comprising the steps of: providing at least one longitudinal element extending between a first portion and a second portion; providing at least one fixation element including a first end and a second end configured for penetrating tissue; providing a deformable collar including a first part and a second part, wherein the parts include an inner surface and an outer surface; disposing the at least one longitudinal element with the collar such that the inner surface of the parts are fixed with the at least one longitudinal element; and inserting the collar within the first end of the at least one fixation element such that the outer surface of the collar snaps in and/or deforms to fit within the first end of the fixation member.

In one embodiment, a method for treating a spine is provided. The method comprises the steps of: providing at least one longitudinal element; providing at least a first fixation element and a second fixation element, each fixation element including a first end and a second end configured for penetrating tissue; providing a first passing instrument and second passing instrument, each instrument defining a perpendicular portion and a distal end including a grabber portion; fastening the first fixation element with a first vertebrae and the second fixation element with a second vertebrae; engaging a first portion of the at least one longitudinal element with the grabber portion of the first passing instrument; passing the at least one longitudinal element through the first end of the first fixation element with the first passing instrument; engaging a second portion of the at least one longitudinal element with the grabber portion of the second passing instrument; and passing the at least one longitudinal element through the first end of the second fixation element with the second passing instrument.

BRIEF DESCRIPTION OF THE DRAWINGS

The present disclosure will become more readily apparent from the specific description accompanied by the following drawings, in which.

Like reference numerals indicate similar parts throughout the figures.

DETAILED DESCRIPTION

The exemplary embodiments of the system and related methods of use are discussed in terms of medical devices for the treatment of musculoskeletal disorders and more particularly, in terms of a spinal correction system. It is envisioned that the system may be employed in applications for correction of deformities, such as, for example, kyphosis and scoliosis. It is contemplated that one or all of the components of the surgical system may be disposable, peel-pack, pre-packed sterile devices. One or all of the components of the system may be reusable. The system may be configured as a kit with multiple sized and configured components.

It is envisioned that the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. It is contemplated that the present disclosure may be employed with other osteal and bone related applications, including those associated with diagnostics and therapeutics. It is further contemplated that the disclosed system may be alternatively employed in a surgical treatment with a patient in a prone or supine position, and/or employ various surgical approaches to the spine, including anterior, posterior, posterior mid-line, direct lateral, postero-lateral, and/or antero-lateral approaches, and in other body regions. The present disclosure may also be alternatively employed with procedures for treating the lumbar, cervical, thoracic and pelvic regions of a spinal column. The system and methods of the present disclosure may also be used on animals, bone models and other non-living substrates, such as, for example, in training, testing and demonstration.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

In one embodiment, a system is provided that facilitates percutaneous, minimally invasive, mini-open and/or open surgery ligament passage. In one embodiment, the system includes a hook or guidewire. In one embodiment, the system includes a malleable tip or malleable hook that is used for engaging a ligament to permit passage in a wide range of ailments. In one embodiment, the system includes a fishhook for engaging a ligament.

In one embodiment, a system is provided for passing a guidewire, ligament, tether and/or other member through a set of screws or other vertebral attachment units. In one embodiment, openings in tissue are created for screw and/or other anchor placement. The system can include a flip-grabber that is passed through the openings. The flip-grabber permits handing off and advancing of a longitudinal element from anchor to anchor. In one embodiment, the system includes tether ends that facilitate attachment of the flip-grabber to a ligament for passing thereof. In one embodiment, the tether ends include butterfly attachments. In one embodiment, the fitted ends can include hooks, magnets, loops and/or grooves.

In one embodiment, the system includes a locking system for percutaneous assembly and modular/stepwise locking. In one embodiment, a deformable collar is provided that is seated around a ligament. The deformable collar is attachable to a pedicle screw and locked into a screw head using compression and/or a snap fit engagement.

In one embodiment, the system of the present disclosure includes a ligament passing funnel clamp. It is contemplated that the system may be employed for percutaneous or minimally invasive ligament passage for multilevel alignment between anchors, such as, for example, bone screws. In one embodiment, a controllable percutaneous instrument is employed to facilitate the direction of a guidewire or ligament lead. In one embodiment, a guide raises or lowers the guidewire. The system can use an instrument having a hook at the end. In one embodiment, a funnel clamp instrument facilitates the holding of a ligament or guidewire.

The following discussion includes a description of a surgical system and related methods in accordance with the principles of the present disclosure. Alternate embodiments are also disclosed. Reference will now be made in detail to the exemplary embodiments of the present disclosure, which are illustrated in the accompanying figures. Turning now to FIGS. 1-11, there is illustrated components of a surgical system, such as, for example, a spinal implant system 20.

The components of system 20 can be fabricated from biologically acceptable materials suitable for medical applications, including metals, synthetic polymers, ceramics, bone material, tissue and/or their composites, depending on the particular application and/or preference of a medical practitioner. For example, the components of system 20, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of system 20 may have material composites, including the above materials, to achieve various desired characteristics such as strength, rigidity, elasticity, compliance, biomechanical performance, durability and radiolucency or imaging preference. The components of system 20, individually or collectively, may also be fabricated from a heterogeneous material such as a combination of two or more of the above-described materials. The components of system 20 may be monolithically formed, integrally connected or include fastening elements and/or instruments, as described herein.

Figure 1:
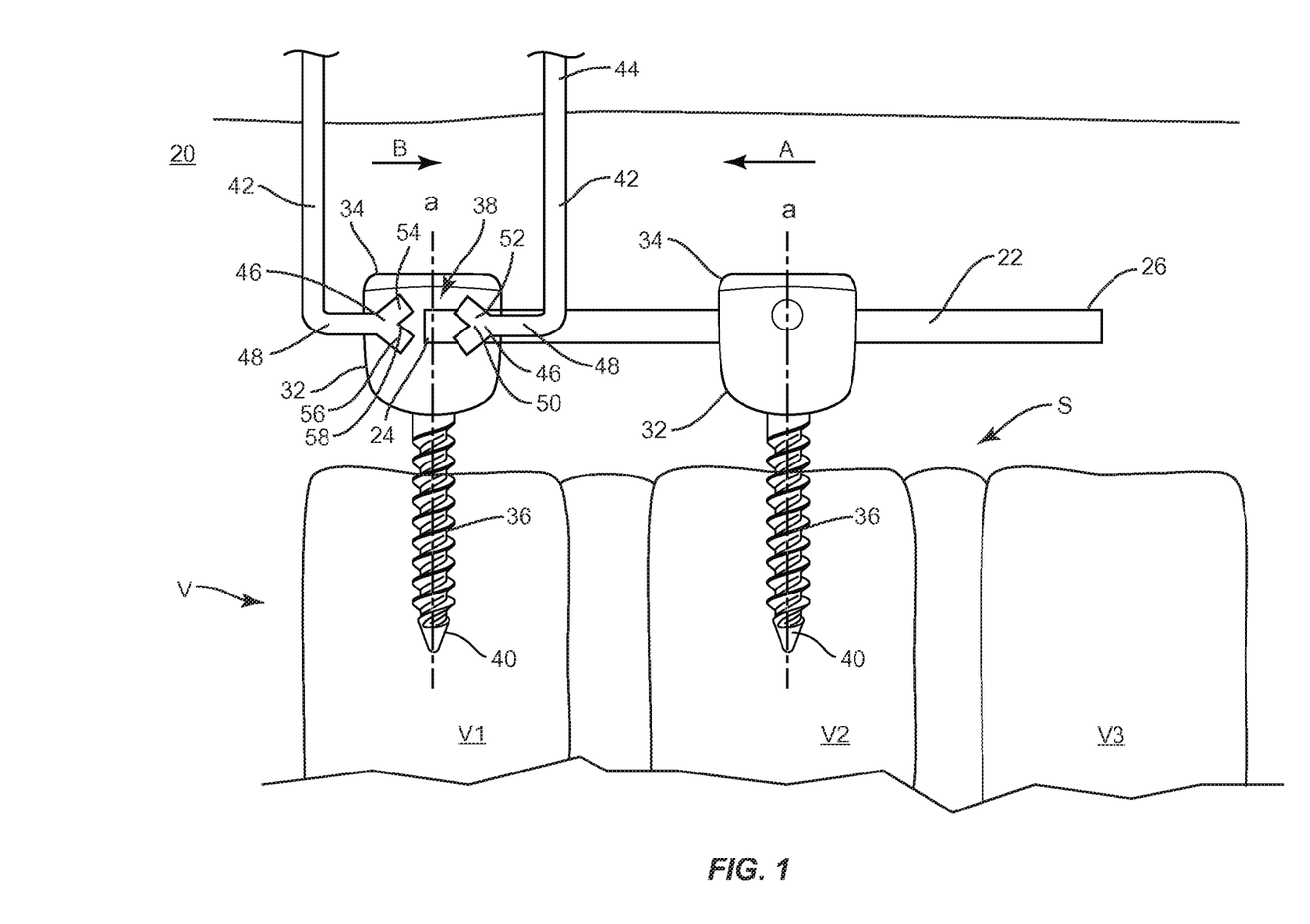
FIG. 1 is a side view of one particular embodiment of a spinal correction system disposed with vertebrae in accordance with the principles of the present disclosure.
Figure 2:
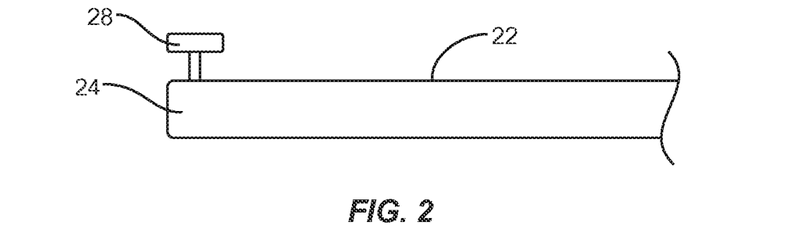
FIG. 2 is a side view of components of the system shown in FIG. 1.

System 20 includes at least one longitudinal element, such as, for example, a ligament 22 extending between a first portion 24 and a second portion 26, as shown in FIG. 1. Portion 24 includes an engagement portion 28, as shown in FIG. 2. Portion 28 is configured for engagement with a passing instrument, as described herein. It is contemplated that portion 28 may be a hook, magnet, loop, butterfly attachment and/or groove. It is further contemplated that one or both of portions 24 and 26 may include engagement portion 28.

Figure 3:
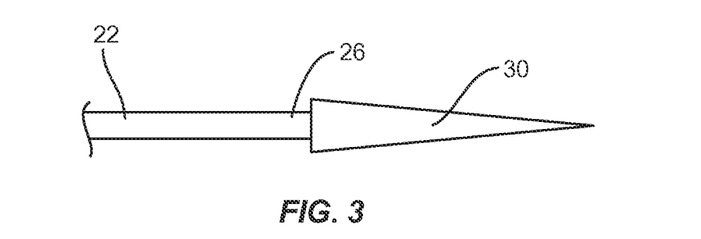
FIG. 3 is a side view of a component of the system shown in FIG. 1.
Figure 4:
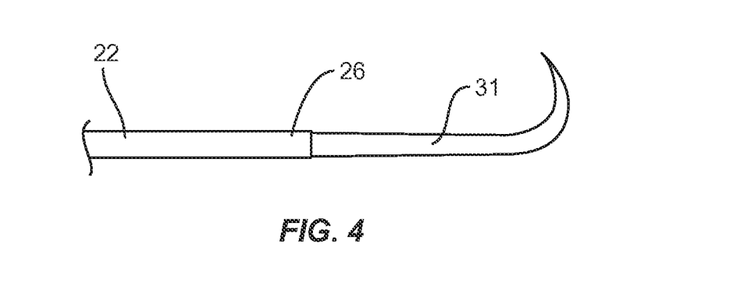
FIG. 4 is a side view of a component of the system shown in FIG. 1.
Figure 5:
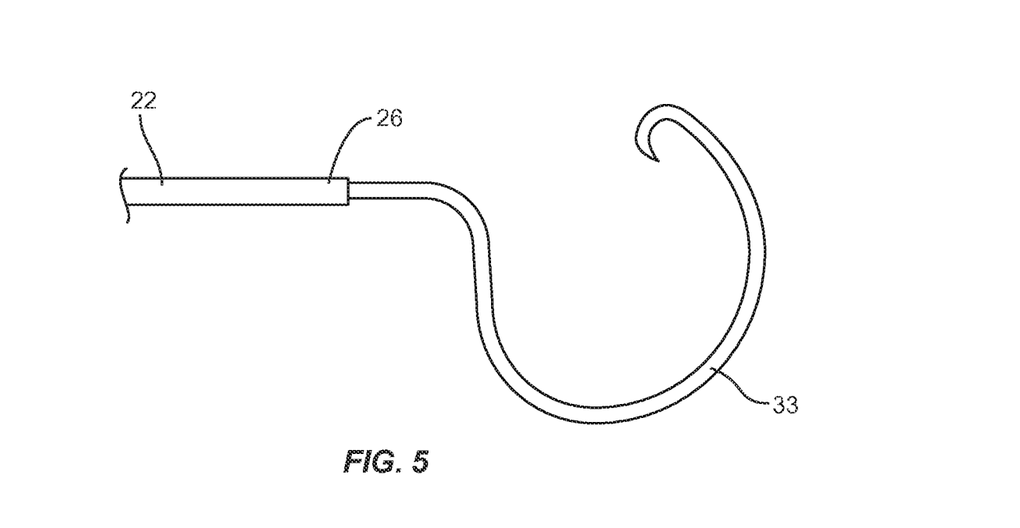
FIG. 5 is a side view of a component of the system shown in FIG. 1.

Portion 26 includes a penetrating member, such as, for example, a tip 30, as shown in FIG. 3. Tip 30 is configured to facilitate ligament 22 passage through a variety of mediums, such as, for example, tissue, bone fasteners and/or other ligaments, as described herein. In one embodiment, tip 30 is malleable. In one embodiment, the penetrating member includes a hook 31, as shown in FIG. 4. In one embodiment, the penetrating member includes a fishhook 33, as shown in FIG. 5. It is further contemplated that the penetrating member may act as a guidewire.

It is contemplated that ligament 22 can have a uniform thickness/diameter. It is envisioned that ligament 22 may have various surface configurations, such as, for example, rough, threaded for connection with surgical instruments, arcuate, undulating, porous, semi-porous, dimpled, polished and/or textured according to the requirements of a particular application. It is contemplated that the thickness defined by ligament 22 may be uniformly increasing or decreasing, or have alternate diameter dimensions along its length. It is further contemplated that ligament 22 may have various cross section configurations, such as, for example, oval, oblong, triangular, rectangular, square, polygonal, irregular, uniform, non-uniform, variable and/or tapered.

It is contemplated that ligament 22 is an implant and may have various lengths, according to the requirements of a particular application. It is further contemplated that ligament 22 may be a rod, tether, braided, such as a rope, or include a plurality elongated elements to provide a predetermined force resistance. It is envisioned that ligament 22 may be made from autograft and/or allograft, and be configured for resorbable or degradable applications. In one embodiment, ligament 22 is a cadaver ligament. In one embodiment, ligament 22 is a ligament that may be harvested, for example, from a patient or donor. It is contemplated that a ligament harvested from a patient may be affixed in remote locations with the patient's body.

In one embodiment, all or only a portion of ligament 22 may have a semi-rigid, rigid or elastic configuration, and/or have elastic and/or flexible properties similar to the properties from materials, such as, for example, fabric, silicone, polyurethane, silicone-polyurethane, copolymers, rubbers, polyolefin rubber, elastomers, thermoplastic elastomers, thermoset elastomers and elastomeric composites. It is contemplated that ligament 22 has a flexible configuration, which includes movement in a lateral or side to side direction. In one embodiment, ligament 22 provides a selective amount of expansion and/or extension in an axial direction. It is further envisioned that ligament 22 may be compressible in an axial direction. Ligament 22 can include a plurality of separately attachable or connectable portions or sections, such as bands or loops, or may be monolithically formed as a single continuous element.

System 20 includes at least one fixation element, such as, for example, a bone screw 32, as shown in FIG. 1. Screw 32 is configured for fixation with ligament 22, as described herein. Screw 32 includes a first end, such as, for example, proximal end 34 and a second end, such as, for example, distal end 36. Screw 32 defines a longitudinal axis a. End 34 includes a receiver that defines an implant cavity 38 configured to receive ligament 22, discussed below. End 36 includes a shaft 40 configured for penetrating tissue.

Shaft 40 has a cylindrical cross section configuration and includes an outer surface having an external thread form. It is contemplated that the thread form may include a single thread turn or a plurality of discrete threads. It is further contemplated that other engaging structures may be located on shaft 40, such as, for example, a nail configuration, barbs, expanding elements, raised elements and/or spikes to facilitate engagement of shaft 40 with tissue, such as, for example, vertebrae.

It is envisioned that all or only a portion of shaft 40 may have alternate cross section configurations, such as, for example, oval, oblong, triangular, square, polygonal, irregular, uniform, non-uniform, offset, staggered, undulating, arcuate, variable and/or tapered. It is contemplated that the outer surface of shaft 40 may include one or a plurality of openings. It is contemplated that all or only a portion of the outer surface of shaft 40 may have alternate surface configurations to enhance fixation with tissue such as, for example, rough, arcuate, undulating, mesh, porous, semi-porous, dimpled and/or textured according to the requirements of a particular application. It is envisioned that all or only a portion of shaft 40 may be disposed at alternate orientations, such as, for example, transverse, perpendicular and/or other angular orientations such as acute or obtuse, co-axial and/or may be offset or staggered. It is further envisioned that all or only a portion of shaft 40 may be cannulated.

System 20 includes at least one passing instrument, such as, for example, passing instrument 42. Instrument 42 includes a proximal end 44 and a distal end 46. End 44 includes a handle portion (not shown). End 46 includes an angled portion 48.

In one embodiment, portion 48 has a perpendicular orientation and defines a 90 degree angle relative to instrument 42. End 46 includes a grabber portion 50. Portion 50 is configured to engage with portion 28 of ligament 22. Portion 50 attaches to portion 28 and advances ligament 22 through vertebral attachment units, such as, for example, cavity 38 of screw 32. Portion 50 defines a clamp 52 that includes a first jaw 54 and a second jaw 56. Jaws 54 and 56 include an inner surface 58 that comprises grooves that are configured for a mating engagement with portion 28 of ligament 22. Portion 50 is configured for releasable fixation with portion 28 for advancing ligament 22.

It is contemplated that portion 50 may be a magnet, hook and/or loop. It is further contemplated that portion 50 may include a nail configuration, barbs, expanding elements, raised elements and/or spikes to facilitate engagement with ligament 22. In one embodiment, instrument 42 is flexible. In one embodiment, a first and a second instrument 42 are used to pass ligament 22 through screw 32, as described herein.

Figure 6:
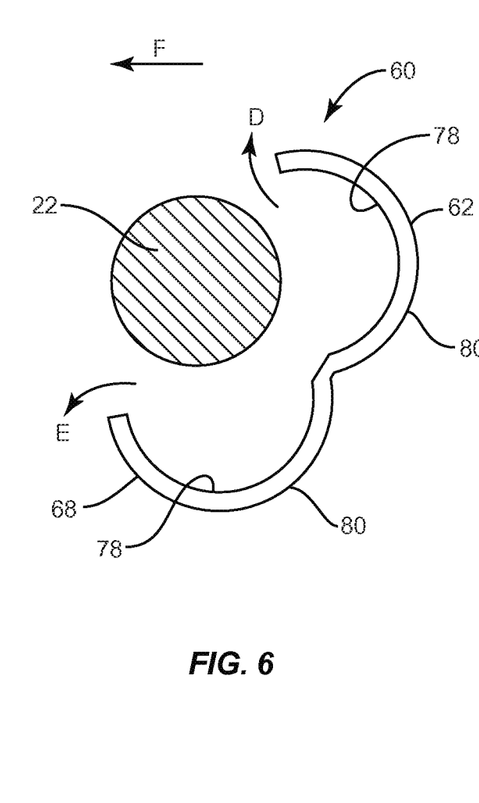
FIG. 6 is a cross-section view of components of the system shown in FIG. 1.
Figure 7:
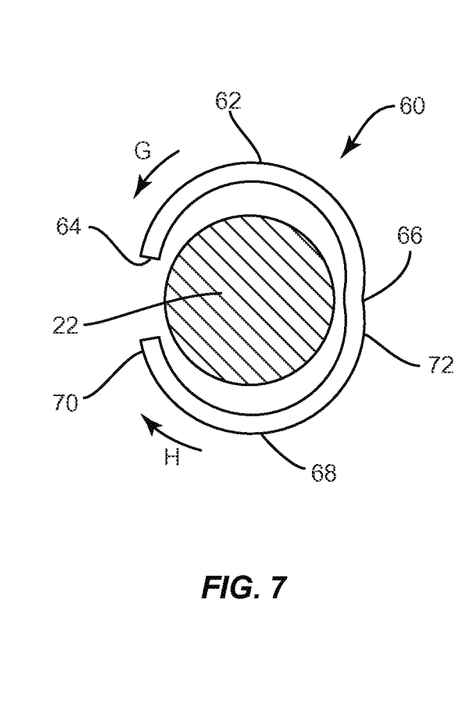
FIG. 7 is a cross-section view of components of the system shown in FIG. 1.
Figure 8:
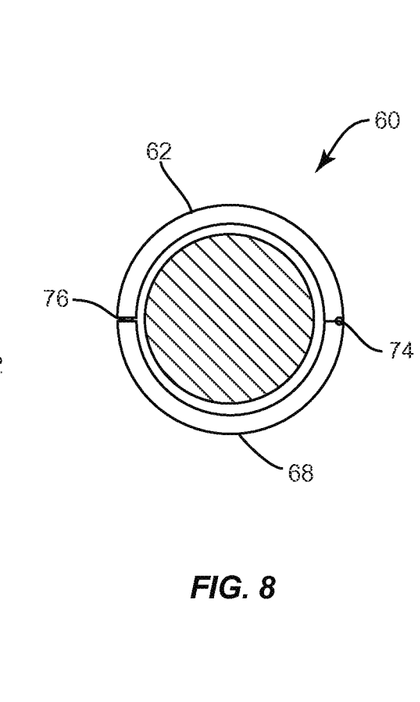
FIG. 8 is a cross-section view of components of the system shown in FIG. 1.

A coupling member, such as, for example, collar 60, as shown in FIGS. 6-8, is configured for disposal about ligament 22 in a first orientation, as described herein. Collar 60 is deformable. Collar 60 includes a first part, such as, for example, a first arm 62. Arm 62 extends between a first end 64 and a second end 66. Collar 60 includes a second part, such as, for example, an arm 68. Arm 68 extends between a first end 70 and a second end 72. In one embodiment, arms 62 and 68 are arcuate shaped. A hinge 74 is pivotably fixed to ends 66 and 72. In one embodiment, hinge 74 is deformable. Arms 62 and 68 lock together at ends 64 and 70 via a locking portion 76. It is contemplated that portion 76 may be a clip, snap closure, magnet, lock and key engagement, staples, adhesive, friction fitting and/or compressive fitting.

Arms 62 and 68 define an inner surface 78. Surface 78 is configured for fixation with ligament 22, as described herein. It is contemplated that surface 78 may be fixed with ligament 22 via adhesive, friction fitting, pressure fit, interlocking keyway, mating parts and/or compressive fitting. Arms 62 and 68 define an outer surface 80. Surface 80 is configured for a snap fit and/or deformable engagement with cavity 38 of screw 32, in a second orientation, as described herein. In one embodiment, surface 80 is configured for a clasp lock engagement with cavity 38, as described herein. It is contemplated that surfaces 78 and 80 may be porous, semi-porous, dimpled, polished and/or textured according to the requirements of a particular application. In one embodiment, the snap fit engagement includes a mechanical joint that attaches collar 60 with screw 32. In one embodiment, the snap fit engagement includes locking features having mating engagement between the components and/or rigid locator features. It is contemplated that the snap fit engagement may be permanent, fixed or releasable. It is further contemplated that collar 60 and screw 32 may cooperatively form a snap fit configuration, such as, for example, cantilever beam, cylindrical or spherical/ball and socket.

In assembly, operation and use, system 20, similar to that described, is employed with a surgical procedure to provide a method for passing a ligament 22, similar to that described above, through fixation elements, such as, for example, at least first and second screws 32. It is contemplated that one or all of the components of system 20 can be delivered or implanted as a pre-assembled device or can be assembled in situ. System 20 may be completely or partially revised, removed or replaced. It is contemplated that one or all of the components of system 20 can be delivered to the surgical site via manual manipulation and/or a free hand technique.

For example, as shown in FIGS. 1-2, system 20 can be employed with a surgical correction treatment of an applicable condition or injury of an affected section of a spinal column and adjacent areas within a body, such as, for example, at least a first vertebrae V1, a second vertebrae V2 and a third vertebrae V3 of vertebrae V. It is envisioned that system 20 may be employed with one or a plurality of vertebrae.

To treat a selected section S of vertebrae V, a medical practitioner obtains access to a surgical site including vertebrae V in any appropriate manner, such as through incision and retraction of tissues. It is envisioned that system 20 can be used in any existing surgical method or technique including open surgery, mini-open surgery, minimally invasive surgery and percutaneous surgical implantation, whereby vertebrae V is accessed through a mini-incision, or sleeve that provides a protected passageway to the area. Once access to the surgical site is obtained, the particular surgical procedure can be performed for treating the spine disorder.

An incision is made in the body of a patient and a cutting instrument (not shown) creates a surgical pathway for implantation of components of system 20. A preparation instrument (not shown) can be employed to prepare tissue surfaces of vertebrae V, as well as for aspiration and irrigation of a surgical region according to the requirements of a particular surgical application.

Pilot holes or the like are made in vertebrae V1, V2, V3 for receiving shafts 40 of screws 32. Screws 32 are fixed with the pilot holes (FIG. 1) via surgical instruments that drive, torque, insert or otherwise connect screws 32 to vertebrae, according to the particular requirements of the surgical treatment.

First instrument 42 connects to ligament 22 via portion 50 and portion 28 of ligament 22. Clamp 52 is attached to portion 28, as described above. Instrument 42 and ligament 22 are inserted into the surgical site. Instrument 42 is advanced in a longitudinal direction, such as, for example, in the direction shown by arrow A in FIG. 1 towards cavity 38 of first screw 32. Instrument 42 passes ligament 22 through cavity 38 of first screw 32.

Second instrument 42 is delivered to the surgical site. Second instrument 42 is disposed at the opposite end of cavity 38. Second instrument 42 is advanced in a second longitudinal direction, such as, for example, in the direction shown by arrow B and is inserted into a portion of cavity 38. Portion 50 of second instrument 42 connects with portion 28 of ligament 22, similar to the first instrument 42 connection to ligament 22 described above. First instrument 42 releases ligament 22. In one embodiment, second instrument 42 attaches to portion 28 of ligament 22 after a portion of ligament 22 has been passed through and has exited out of cavity 38. Second instrument 42 is moved in the direction shown by arrow A such that second instrument 42 and ligament 22 translate through cavity 38. Ligament 22 is passed out of cavity 38. Ligament 22 is advanced and passed through second screw 32, in a manner similar to ligament 22 and first screw 32 described above.

In one embodiment, system 20, similar to that described, is employed with a surgical procedure to provide a method for treating a spine, which includes attaching a longitudinal element, such as for example, ligament 22 with a fixation element, such as, for example, screw 32, via a collar 60, similar to that shown and described with regard to FIGS. 6-11. A medical practitioner obtains access to a surgical site in a manner similar to that described above. Screws 32 are fixed to vertebrae V, similar to that described above. Locking portion 76 of collar 60 is opened, spreading arms 62 and 68 open and apart at ends 64 and 70, in the direction shown by arrows D and E in FIG. 6. Ligament 22 is placed adjacent collar 60. Collar 60 is advanced in a longitudinal direction, such as, for example, in the direction shown by arrow F towards ligament 22 and arms 62 and 68 are drawn and/or compressed together, in the direction shown by arrows G and H in FIG. 7. Arms 62 and 68 are locked at portion 76, which fixes ligament 22 with inner surface 78 of arms 62 and 68, placing collar 60 in a first orientation with ligament 22.

Figure 9:
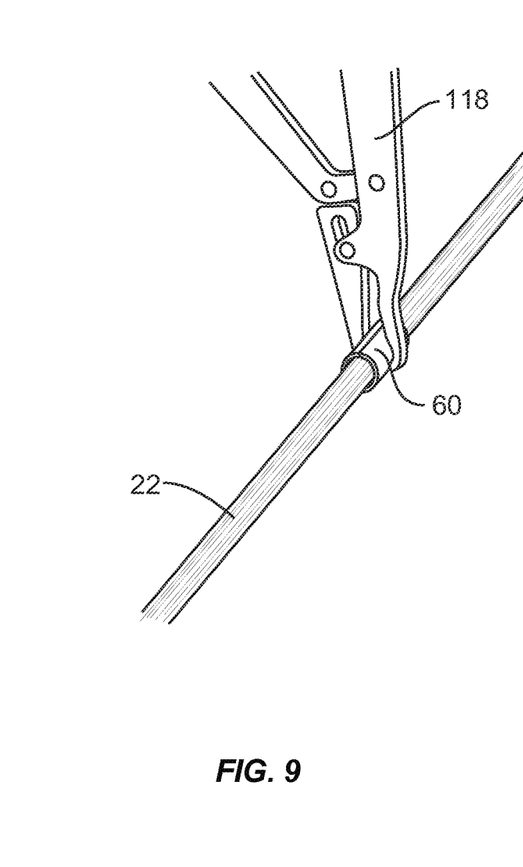
FIG. 9 is a perspective view of components of the system shown in FIG. 1.
Figure 10:
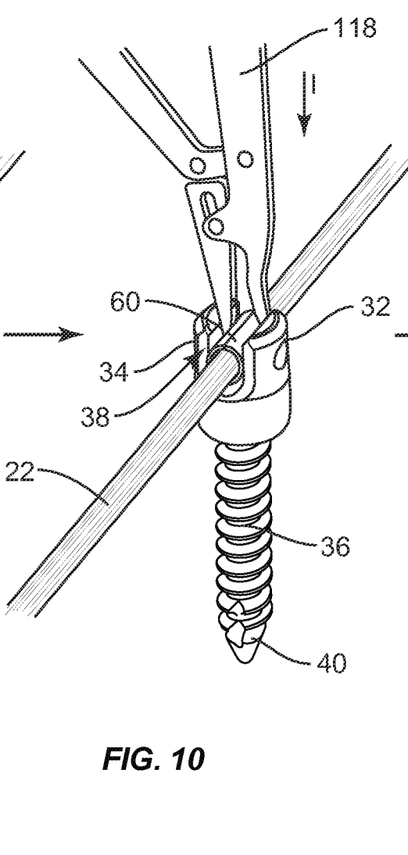
FIG. 10 is a perspective view of components of the system shown in FIG. 1.
Figure 11:
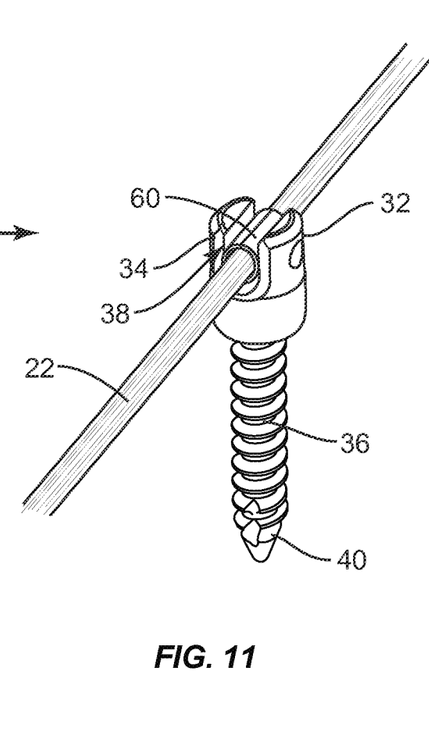
FIG. 11 is a perspective view of components of the system shown in FIG. 1.

An instrument 118, as shown in FIG. 9, grasps outer surface 80 of collar 60 to facilitate movement and placement of ligament 22 and collar 60 with screw 32. Instrument 118 positions collar 60 above cavity 38 of screw 32, as shown in FIG. 10. Instrument 118 is pushed, in the direction shown by arrow I, which delivers collar 60 within cavity 38, disposing collar 60 in a second orientation. In the second orientation, outer surface 80 of collar 60 snaps in and/or deforms to fit within cavity 38, as shown in FIG. 11. Collar 60 fixes ligament 22 with screw 32 for implantation of the components of system 20 with vertebrae V. In one embodiment, collar 60 engages screw 32 to permanently fix ligament 22 with screw 32. In one embodiment, collar 60 engages screw 32 to releasably fix ligament 22 with screw 32. Upon completion of the procedure, the non-implant components of system 20 are removed from the surgical site and the incision is closed.

In one embodiment, system 20 includes an agent, which may be disposed, packed or layered within, on or about the components and/or surfaces of system 20. It is envisioned that the agent may include bone growth promoting material, such as, for example, bone graft to enhance fixation of the fixation elements with vertebrae V. It is contemplated that the agent may include one or a plurality of therapeutic agents and/or pharmacological agents for release, including sustained release, to treat, for example, pain, inflammation and degeneration. The components of system 20 can be made of radiolucent materials such as polymers. Radiomarkers may be included for identification under x-ray, fluoroscopy, CT or other imaging techniques. It is envisioned that the use of microsurgical and image guided technologies may be employed to access, view and repair spinal deterioration or damage, with the aid of system 20.

Figure 12:
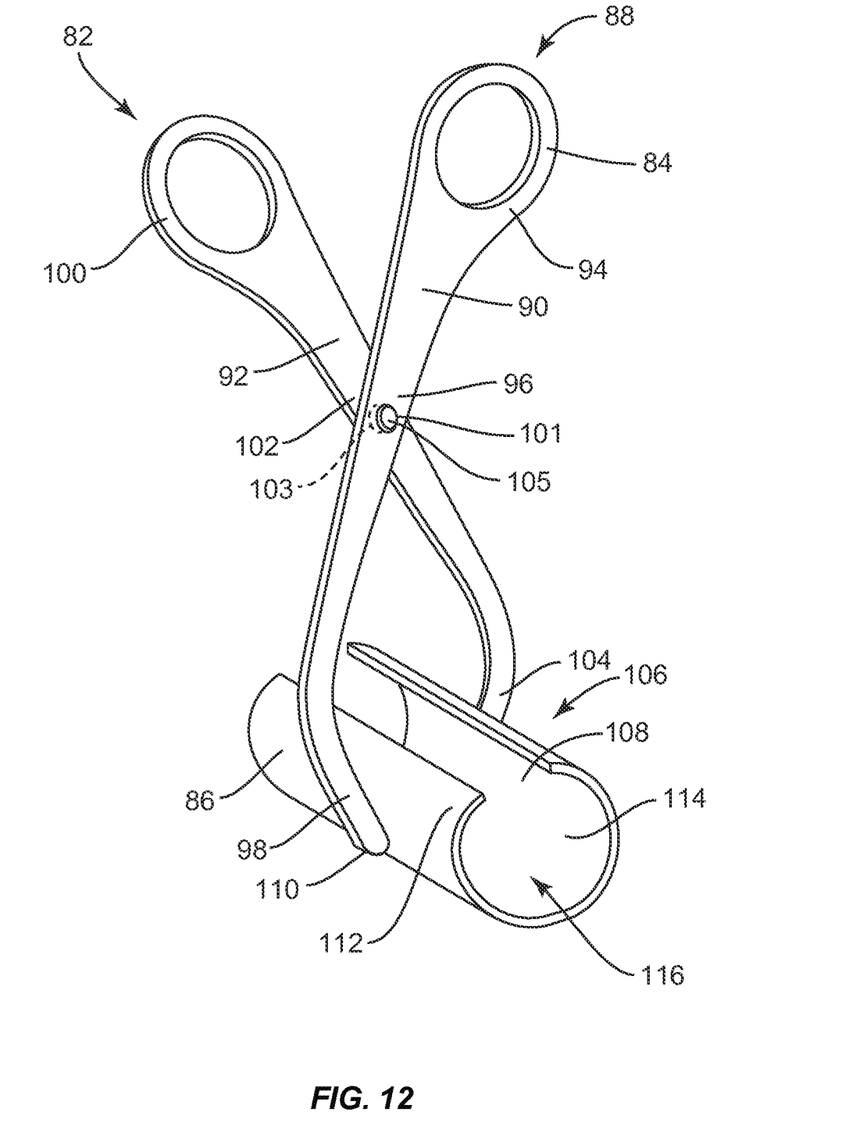
FIG. 12 is a perspective view of one embodiment of a system in accordance with the principles of the present disclosure.
Figure 13:
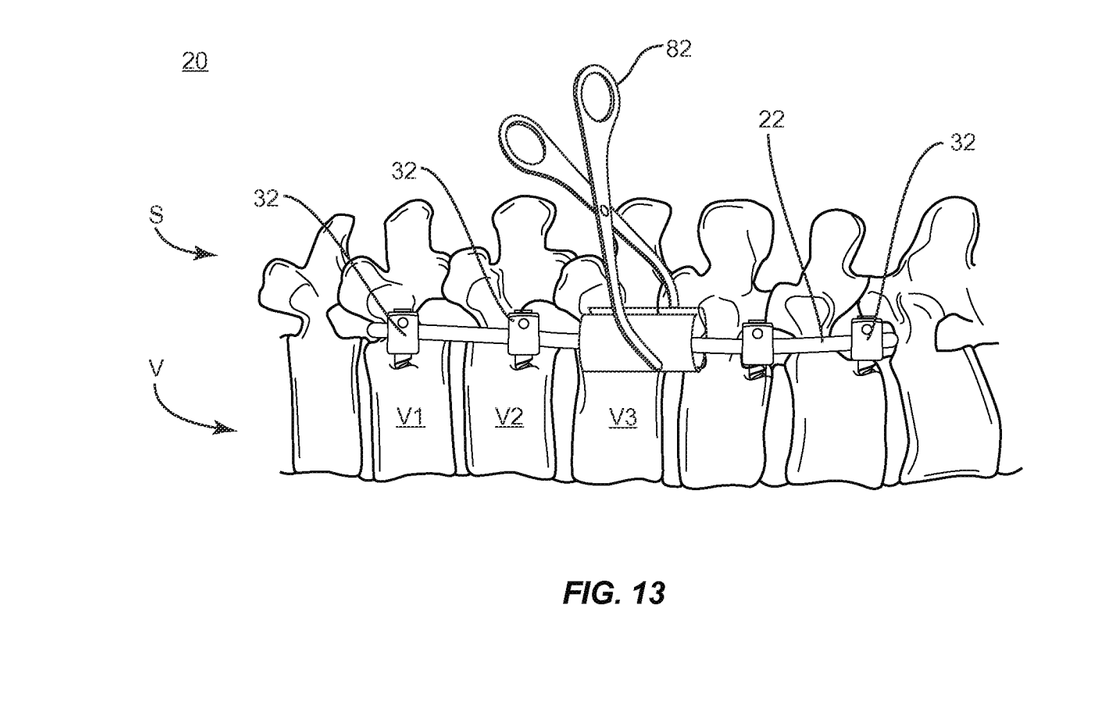
FIG. 13 is a side view of components of the system shown in FIG. 12 disposed with vertebrae.

In one embodiment, as shown in FIG. 12, system 20 includes a clamping instrument 82. Instrument 82 is configured for engagement with ligament 22, as described herein. It is contemplated that instrument 82 holds ligament 22 in position during a surgical procedure. In one embodiment, instrument 82 is configured to support and/or manipulate ligament 22 during a spinal procedure, as shown in FIG. 13. It is further envisioned that instrument 82 may engage with other longitudinal elements, such as, for example, a rod, guidewire and/or tether. Instrument 82 extends between a proximal end 84 and a distal end 86. End 84 includes a handle 88. A portion of a first extension 90 and a second extension 92 define handle 88. Extension 90 includes a proximal end 94, an intermediate portion 96 and a distal end 98. Extension 92 includes a proximal end 100, an intermediate portion 102 and a distal end 104. Ends 94 and 100 define handle 88. Ends 94 and 100 are loops. It is contemplated that the shape of ends 94 and 100 may be variously configured according to the requirements of a particular application.

Extensions 90 and 92 pivotably engage at portions 96 and 102. Portions 96 and 102 include openings 101 and 103 respectively. Openings 101 and 103 are configured for engagement with a biasing member, such as, for example, a pin 105. Pin 105 facilitates movement of extensions 90 and 92.

End 84 includes a support member 106. Member 106 defines a first surface 108 and a second surface 110. Surface 108 is connected to extension 90 via end 98. Surface 110 is connected to extension 92 via end 104. Surfaces 108 and 110 movably engage with via expansion and contraction of extensions 90 and 92. Member 106 includes a convex outer surface 112 and a concave inner surface 114. A hollow channel 116 is defined by surface 114. Channel 116 is configured to engage with ligament 22, as described herein.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A spinal implant system comprising:
   at least one longitudinal element extending between a first portion and a second portion;
   at least one fixation element extending a longitudinal axis between a first end and a second end configured for penetrating tissue; and
   a coupling member configured for disposal about the at least one longitudinal element, the coupling member including a first part and a second part being movable relative to the first part between a first orientation and a second orientation such that an inner surface of the parts are fixed with the at least one longitudinal element, the parts including an outer surface such that in the second orientation the coupling member is configured for a snap fit engagement with the at least one fixation element such that the coupling member is prevented from translating along the longitudinal axis.

2. A spinal implant system as recited in claim 1, further comprising a clamping instrument extending between a proximal end and a distal end defining a support member.

3. A spinal implant system as recited in claim 2, wherein the support member is hollow and configured to support the at least one longitudinal element.

4. A spinal implant system as recited in claim 1, further comprising at least one passing instrument defining a perpendicular portion and a distal end including a grabber portion.

5. A spinal implant system as recited in claim 4, wherein at least the first portion of the longitudinal element includes an engagement portion extending therefrom configured to connect with the grabber portion.

6. A spinal implant system as recited in claim 5, wherein the engagement portion includes a hook, magnet, loop, butterfly attachment and/or groove.

7. A spinal implant system as recited in claim 1, wherein the second portion of the longitudinal element includes a penetrating member.

8. A spinal implant system as recited in claim 7, wherein the penetrating member is a malleable hook or guidewire.

9. A spinal implant system as recited in claim 1, wherein the coupling member is a deformable collar.

10. A spinal implant system as recited in claim 1, wherein the coupling member is deformable from the first orientation to the second orientation.

11. A spinal implant system as recited in claim 1, wherein the first part and the second part of the coupling member are arcuate shaped.

12. A spinal implant system as recited in claim 1, wherein the coupling member includes a hinged connection that pivotably connects the first part with the second part.

13. A spinal implant system as recited in claim 12, wherein the hinged connection is deformable.

14. A spinal implant system as recited in claim 1, wherein in the second orientation, the outer surface of the coupling member is configured for engagement with the at least one fixation element such that the coupling member and the at least one fixation element form a compression fitting that locks the coupling member with the at least one fixation element.

15. A method for treating a spine, the method comprising the steps of:
- providing at least one longitudinal element extending between a first portion and a second portion;
- providing at least one fixation element extending along a longitudinal axis between a first end and a second end configured for penetrating tissue;
- providing a deformable collar including a first part and a second part, wherein the parts include an inner surface and an outer surface;
- disposing the at least one longitudinal element with the collar such that the inner surface of the parts are fixed with the at least one longitudinal element; and
- inserting the collar within the first end of the at least one fixation element such that the outer surface of the collar snaps to fit within the first end of the fixation member to prevent the collar from translating along the longitudinal axis.

16. A method for treating a spine as recited in claim 15, further comprising the step of providing an instrument for engaging the collar to fit the collar within the first end of the fixation member.

17. A method for treating a spine as recited in claim 15, wherein the step of disposing the at least one longitudinal element with the collar includes applying a force to crimp the collar with the at least one longitudinal element.

18. A method for treating a spine, the method comprising the steps of:
- providing at least one longitudinal element;
- providing at least a first fixation element and a second fixation element, each fixation element including a first end and a second end configured for penetrating tissue;
- providing a first passing instrument and second passing instrument, each instrument defining a perpendicular portion and a distal end including a grabber portion;
- fastening the first fixation element with a first vertebrae and the second fixation element with a second vertebrae;
- engaging a first portion of the at least one longitudinal element with the grabber portion of the first passing instrument;
- passing the at least one longitudinal element through the first end of the first fixation element with the first passing instrument;
- engaging a second portion of the at least one longitudinal element with the grabber portion of the second passing instrument; and
- passing the at least one longitudinal element through the first end of the second fixation element with the second passing instrument.

19. A method for treating a spine as recited in claim 18, wherein the step of engaging a second portion includes releasing the at least one longitudinal element from the first passing instrument.

20. A method for treating a spine as recited in claim 18, wherein the step of passing includes passing the at least one longitudinal element through the first end of the first fixation element.

* * * * *